| United States Patent [19] | [11] 4,018,842 |
|---|---|
| Canova | [45] Apr. 19, 1977 |

[54] SELECTIVE HYDROGENATION OF α-PINENE TO cis-PINANE

[75] Inventor: Levy A. Canova, Orange Park, Fla.

[73] Assignee: SCM Corporation, New York, N.Y.

[22] Filed: May 27, 1976

[21] Appl. No.: 690,558

[52] U.S. Cl. .................. 260/675.5; 260/666 PY
[51] Int. Cl.² ................ C07C 5/14; C07C 13/32
[58] Field of Search ...... 260/675.5, 677 H, 666 PY

[56] References Cited

UNITED STATES PATENTS 3,240,821   3/1966   Ohloff et al. .................. 260/631.5

OTHER PUBLICATIONS

Bull. Soc. Chem. 10 (657) pp. 4141–4145 (1968).

*Primary Examiner*—Delbert E. Gantz
*Assistant Examiner*—G. E. Schmitkons
*Attorney, Agent, or Firm*—Richard H. Thomas

[57] ABSTRACT

Disclosed is a process for the stereoselective hydrogenation of α-pinene to cis-pinane in which the formation of trans-pinane is suppressed. The hydrogenation is carried out in the presence of a hydrogenation catalyst, under hydrogenation conditions, wherein to obtain increased stereoselectivity, an effective amount of the reactive surfaces of the hydrogenation catalyst is inactivated with a catalyst modifier.

5 Claims, No Drawings

SELECTIVE HYDROGENATION OF α-PINENE TO cis-PINANE

The present invention relates to the stereoselective hydrogenation of α-pinene to cis-pinane.

For purposes of the present application, stereoselectivity means that synthesis that produces one diastereoisomer (or diastereoisomeric dl pair) of a given structure in considerable predominance over all other possible diastereoisomers (or diastereoisomeric dl pair) of the same structure.

BACKGROUND OF THE INVENTION

A principal value of cis-pinane lies in the synthesis of linalool. The reaction sequence from α-pinene to linalool is illustrated in the following equation.

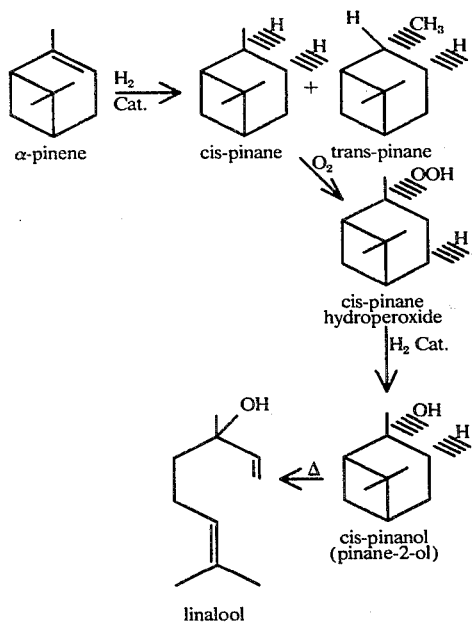

The reaction sequence to cis-pinanol is disclosed in Bull. Soc. Chem., Vol. 10 (No. 657), pp. 4141–4145 (1968), the subject matter of which is incorporated by reference herein. The pyrolysis to linalool may be found in U.S. Pat. No. 3,240,821, Ohloff et al, also incorporated by reference herein. Preferably, the hydrogenation of α-pinene to pinane is carried out under pressure over a nickel catalyst, and the product mixture, after separation from the catalyst, is oxidized with elemental oxygen in the presence of azobisisobutyronitrile to produce pinane hydroperoxide. This product mixture is then subjected to reduction in the presence of hydrogen and a catalyst to reduce the hydroperoxide to pinanol which is pyrolyzed to linalool.

In the above oxidation and reduction steps, there is formed some trans-pinane hydroperoxide and trans-pinanol in the ratio of about 80 cis-:20 trans-. For the sake of simplicity, only the predominant cis- forms are shown. In the pyrolysis step, both the cis- and trans-pinanol are pyrolyzed to linalool.

A primary problem in the reaction sequence is that, in the oxidation to the hydroperoxide, the cis-pinane oxidation occurs at a much faster rate than the trans-pinane oxidation, on the order of about 10:1. (Reported by Fisher et al* and confirmed by Applicant's observations.) The oxidation could be allowed to run to substantial completion and oxidation of trans-pinane, but during the oxidation step, decomposition of the hydroperoxide product occurs which increases with increased concentration of the hydroperoxide and by-products of the oxidation reaction. This necessitates stopping the reaction as a practical matter at about 50% conversion of the pinane. Distillation of the product mixture is then carried out and unreacted pinane is recycled for addition to fresh pinane and further oxidation.

*JACS, 75- 3675-3678 (1953).

Fortunately, the initial hydrogenation step is stereoselective in favor of cis-piane so that the recycled unreacted pinane mixture from the oxidation step contains only a small amount of the less-readily oxidizable trans-pinane. Even so, it is apparent that after multiple recycles; e.g., 5 or 6, the recycle will contain a sufficiently high level of trans-pinane to require its disposal or purge. This purge is accomplished by accumulating the high-trans containing recycle material over a substantial period of time and then subjecting the same to successive oxidation and reduction steps, without addition of fresh pinane, each time producing additional hydroperoxide and consuming or reducing cis-pinane content, until the cis-pinane:trans-pinane ratio reduces to about 50:50.

At this point reoxidation of the pinane mixture is terminated, and the pinane is disposed of with an obvious purge of still unreacted cis-pinane. The cis- and trans-pinanes are inseparable by fractional distillation, so that this represents a substantial loss of desired cis-pinane.

The hydrogenation of α-pinene to cis- and trans-pinane has heretofore been carried out using a nickel hydrogenation catalyst, such as a supported catalyst Girdler G-69 (trademark, Girdler Chemicals, Inc.); or a Raney nickel catalyst (trademark, W. R. Grace & Co.) which is unsupported. Also, a partly colloidal Rufert nickel catalyst (for instance, Ni-5000 F, Harshaw Chemical Company, trademark) can be employed. The present invention is applicable to any nickel catalyst conventionally used in the hydrogenation of olefinic bonds, although it will be apparent that the present invention is primarily applicable to the use of the supported and Raney nickel catalysts.

In the conventional hydrogenation of α-pinene, selectivity to cis-pinane is experienced, which varies depending upon temperature and reaction time, the selectivity being better at lower temperature and longer reaction time. In this regard, Applicant's experience has been that a typical cis-:trans-ratio will vary from about 87:13 (for about 2 hours' reaction time) to a maximum of about 95:5 for longer reaction times, for instance about 14 hours. Up to 30 or more hours' reaction time is reasonable. Use of a Rufert catalyst may result in increased cis-:trans-ratios, but the use of this catalyst has the disadvantage that it cannot be separated from the reaction products by simple filtration, requiring distillation or clay treatment for complete removal of nickel from the reaction mixture.* The removal of the nickel is necessary as it tends to cause acceleration of the decomposition of the pinane hydroperoxide to undesirable products during the oxidation step.

* Catalysis, Vol. III, page 426, Paul H. Emmett, Reinhold Publishing Corporation, 1955.

SUMMARY OF THE INVENTION

The present invention resides in the discovery that in a process for the hydrogenation of α-pinene to cis-pinane, with elemental hydrogen, in the presence of a hydrogenation nickel catalyst, under hydrogenation conditions, stereoselectivity in favor of cis-pinane product with good conversion is substantially increased by inactivating an effective amount of the reactive surfaces of the hydrogenation catalyst, effective being defined as that amount necessary to achieve increased stereoselectivity.

By the present invention, stereoselectivity in favor of the cis-pinane can be obtained on the order of about 98:2 or better, in the hydrogenation of α-pinene. This represents more than a 100% improvement in reducing the amount of trans-pinane formed, over conventional ratios which at best were about 95:5. In addition, this results in a substantial reduction in loss of desired cis-pinane on purge, following oxidation of the pinane. It will be recalled that the high-trans containing accumulated recycle material which is accumulated after multiple recycles of unreacted pinane mixture from the oxidizing step also contains cis-pinane, in the ratio of approximately 50:50. The cis-pinane and trans-pinane are not readily separable (for instance, they are inseparable by fractional distillation) and purge of the trans-pinane thus results in purge of about the same amount of cis-pinane.

Although the nickel catalyst conventionally used in the hydrogenation of olefinic bonds can be employed in the process of the present invention, a catalyst such as a Rufert catalyst (a partly colloidal nickel catalyst sold under the trademark Ni-5000 F, by Harshaw Chemical Company) is not preferred. Again, this catalyst is not capable of separation by simple filtration from the reaction products and distillation of clay treatment is required for complete removal of nickel from the reaction mixture. Accordingly, the present application in its preferred aspects is limited to filtratable nickel catalysts.

A preferred nickel catalyst for use in the hydrogenation process of the present invention is a supported nickel catalyst, such as Girdler G-69 (registered trademark), a nickel catalyst which is zirconium promoted nickel on Kieselguhr, 55% nickel and 2% zirconium, or Girdler G-210 (trademark), also a supported and promoted nickel catalyst. Another suitable catalyst is Harshaw 1404P (registered trademark) which is 68% nickel on a proprietary support. Another supported catalyst is Calsicat 210P (trademark). A Raney nickel catalyst can also be employed. Suitable Raney nickel-type catalysts are those marketed by W. R. Grace & Co. under the trademarks "Raney 28" and "Raney 30". The term "Raney" is indicated to be a registered trademark of W. R. Grace & Co. However, it is used generically in the art to indicate a class of catalysts, used for purposes of this application, it is also so used. Another suitable nickel catalyst of the Raney type is a "sponge" nickel catalyst marketed by Activated Metals, Inc., under the trademark "A-5000". Other such catalysts are those prepared in accordance with the procedures set forth in "Organic Syntheses Collective Volume 3", John Wiley & Sons, New York, copyright 1955, pages 176 plus. (This publication is incorporated by reference herein.)

The advantage in use of a supported catalyst is its initial activity at lower temperatures. Improved selectivities are obtained at lower temperatures, in the order of 50°–70° C., although higher temperatures, such as 100°–150° C., can be employed in the hydrogenation reaction. Higher temperatures afford shorter reaction times, but lower temperatures provide increased selectivity.

The nickel catalyst can have a substantial portion of its reactive surfaces deactivated by employing any of a large number of catalyst modifiers. The modifier should be non-toxic to the catalyst, toxic being defined as that effect which results in substantial killing of the catalyst, or a substantial reduction in reaction rate and/or yield, particularly at the level of use of an effective amount of the modifier. It is, of course, understood that a satisfactory rate of conversion and/or yield is primarily a matter of economics and can vary widely with or is dependent upon such factors as equipment size, throughput, catalyst level, catalyst cost, and reusability. Still, those agents or compounds which are toxic to the catalyst are either well-known or can be determined by routine experimentation, and the same are not within the scope of the present invention. It should also be evident that the modifying agent should not be one which when used in an effective amount is reactive with the cis-pinane or other products of the reaction sequence. Modifying agents which are within the scope of the present invention are elemental halogen or halogen-containing compounds, preferably organic halogen compounds, for ease of operation. One particular modifying agent is hydrogen chloride. Organic halide modifiers within the scope of the present invention include carbon tetrachloride ($CCl_4$); ethylene dichloride; methylene trichloride, ($CHCl_3$); methylene tribromide ($CHBr_3$); ethylene dibromide ($CH_2Br_2$); carbon tetrabromide ($CBr_4$); carbon bromide trichloride ($CBrCl_3$); iodene counterparts of the above; 3-chloropropene; 3-bromopropene; trichloroacetic acid; 1,2-dichloroethane; chloroacetone; 2-chloroethanol; chlorobenzene; o-chlorotoluene; p-chlorophenol; p-chloroacetophenone; hydrogen chloride and benzoyl chloride. Particular elemental halogen compounds within the scope of the present invention include elemental chlorine and elemental bromine.

An inorganic modifier may also be employed, such as inorganic metal salts from Group I to VIII (preferably Periods 4 through 7 and the Rare Earths) of the Periodic Table. Specific such metal salt modifiers include cupric chloride ($CuCl_2$); and nickel chloride ($NiCl_2.6H_2O$). Others are $AlCl(i-PrO)_2$*; and $Al(OH)(OAc)_2$; $Cu(OAc)_2$; $CuSo_2$; $CuBr_2$; $SrCl_2$; $ZnCl_2$; $ZnSO_4$; $Zn(OAc)_2.2H_2O$; $ZnBr_2$; $CdCl_2$; $HgCl_2$; $TiCl_3$; $Ti_2(C_2O_4)_3$; $SnCl_4$; $VBr_3$; $CrCl_3.6H_2O$; $MoCl_5$; $Mn(OAc)_2.4H_2O$; $MnSO_4.H_2O$; $Fe(OH)(OAc)_2$; $FeBr_3$; $CoCl_2$; $Co(OAc)_2.4H_2O$; $NiSo_4$; $NiBr_2.6H_2O$; $NiI_2.6H_2O$; $RuCl_2$; and $SmCl_3$.

*"i-PrO" means the isopropoxy radical; "OAc" means the acetate radical.

The catalyst treatment may be carried out prior to hydrogenation by slurrying the catalyst with a small amount of α-pinene or other vehicle, and then adding the modifier, such as hydrogen chloride, to the slurry. The slurry is then added to the principal reactant which can be the bulk of the α-pinene. Obviously, any hydrocarbon could be employed as a vehicle to slurry the catalyst and modifier, although the use of α-pinene or pinane avoids the addition of impurities to the reaction mixture. Either cis- or trans-pinane also can be employed as the vehicle for the catalyst. Alternatively, the modifier can be added or included in the pinene feed added to the nickel catalyst bed.**

**Other techniques for modification of the nickel catalyst are within the skill of those in the art.

In the case of elemental chlorine, a convenient way to treat the nickel catalyst is to add to the pinene a halogenating agent such as sodium hypochlorite. The chlorine reacts with the double bond of pinene and modification of the nickel catalyst occurs with mixing of the pinene and catalyst.

The proportion of catalyst employed in the hydrogenation is not particularly critical and is dictated by conventional hydrogenation practice. The catalyst range can vary from a minimum of about 0.02%, based on the weight of pinene, up to 10–15% or even 20%. A preferred range is in the order of about 0.2%–3%. Particularly preferred is 2 ½% catalyst based on pinene feed.

The amount of modifier should be sufficient to effect a stereochemical improvement, and yet less than that amount which substantially adversely affects reaction rate and conversion; i.e., having a substantial toxic effect on the catalyst. In this regard, it is believed that the anions of the modifier molecule are primarily responsible in the modifying action so that the amount of modifier employed may vary somewhat depending upon the number of anions in the modifier molecule. Experimentation is required, employing conventional modifying agents, to determine the optimum level of inactivation required, or optimum stereoselectivity obtained. Obviously, excessive modifier may adversely and excessively affect reaction rate and/or yield, and the upper limit of modifier is readily determined by such experimentation.

Conventional hydrogenation conditions may be employed in the hydrogenation process. For instance, it was found that pressure did not significantly affect the cis-/trans- ratio. More than doubling the hydrogen pressure (about 3oo to about 800 psig) had no significant effect on the reaction rate or product ratio. A preferred temperature range with conventional hydrogenation nickel catalysts is between about 30°–150° C. with about 50°–80° C. being particularly preferred.

The invention will become apparent from the following examples. In the examples, it is understood that all percentages are percentages by weight and temperatures are in degrees Centigrade, unless otherwise stated. Pressure is in pounds per square inch gauge. Time is in hours.

EXAMPLE 1

A 500 gram sample of "0" PPM sulfur α-pinene was stirred with 50 ml of an aqueous solution containing 2.5% sodium hypochlorite for 15 minutes. The pinene was then separated from the aqueous solution, washed with tap water, and dried with MgSO$_4$. This dried α-pinene containing trace amounts of organic chlorine was placed in a Parr bomb with 15 grams Girdler G-69 catalyst (nickel on Kieselguhr, which analyzed 55% Ni, 2% zirconium). This mixture was stirred under 200 lb./in.$^2$ hydrogen at room temperature (30° C.). After stirring for 19 hours the reaction temperature was increased to 60° C. and held at 60° C. for 6 more hours. The product was analyzed by vapor phase chromatography and was found to contain pinane and about 2.97% trans-pinane). Hydrogenation under similar conditions but using α-pinene free of both sulfur and chloride gave a product containing at best 4 to 5% trans-pinane and 93–95% cis-pinane.

The reduction from 4–5% trans- to 2.97% trans- is significant. As previously indicated, only the cis-pinane is readily oxidizable to pinane hydroperoxide, and oxidation is carried only to about 50% conversion. The remainder is recycled until a high trans-pinane content is obtained, followed by purge, in which a loss of an approximately equal amount of cis-pinane occurs. Total improvement thus becomes the sum of additional pinene conversion to cis-pinane plus reduction in cis-pinane lost in the purge.

EXAMPLE 2

This example illustrates the hydrogenation of α-pinene employing different modifiers and different hydrogenation conditions. The α-pinene in the run employing HCl as the modifier was obtained from a pilot plant hydrogenation reaction and contained about 69% α-pinene. The starting composition in the remaining runs was approximately as follows:

95.7–96.9% α-pinene
0.4–0.6% tricyclene
1.1–1.3% β-pinene
1.4–1.9% camphene.

The feed in all instances was made substantially sulfur-free to avoid killing the catalyst.

The runs were all carried out in a Monel Parr bomb, purged with nitrogen and then with hydrogen. The reactants, in the proportions indicated in the following Table I, were charged to the bomb, which was then heated to about 50° C. and pressurized with hydrogen to about 4000 psig, with stirring throughout. The temperature was then maintained at the level indicated, and at the pressure indicated, to completion of the reaction as determined by vapor phase chromatographic analysis of a filtered sample. The results are given in the following Table I.

In the table, the weight of catalyst and modifier are based on α-pinene weight. In all cases, the catalyst modifier was added to the α-pinene feed. In the case of the hypochlorite treatment, this was carried out with a 5% solution of sodium hypochlorite added in the amount of 10% based on the weight of pinene feed followed by stirring, water washing and drying with MgSO$_4$. Time is in hours and temperatures is in degrees Centigrade. The sub-headings mean the following:

αP means α-pinene
cP means cis-pinane
tP means trans-pinane
c/t means cis-:trans-pinane ratio The term "Heel" indicates reuse of the catalyst from a previous hydrogenation reaction.

TABLE I

| α-PINENE HYDROGENATIONS WITH G-69 CATALYST AND VARIOUS MODIFYING AGENTS | | | | | | | | |
|---|---|---|---|---|---|---|---|---|
| Catalyst | Start. Matl. | Time | Temp. | H$_2$ Press. | α-P | cP | tP | c/t |
| CUPRIC CHLORIDE | | | | | | | | |
| G-69 (3%) | α-Pinene + 0.05% CuCl$_2$ | 24 | 45–63 | 400 | 10.3 | 86.1 | 2.8 | 96.9/3.1 |
| Heel (3%) | α-Pinene | 64–½ | 46–57 | 400 | 0.4 | 96.8 | 2.1 | 97.9/2.1 |

TABLE I-continued
α-PINENE HYDROGENATIONS WITH G-69 CATALYST AND VARIOUS MODIFYING AGENTS

| Catalyst | Start. Matl. | Time | Temp. | H₂ Press. | α-P | cP | tP | c/t |
|---|---|---|---|---|---|---|---|---|
| HYPO-TREATMENT | | | | | | | | |
| G-69 (3%) | Hypo-treated α-pinene | 8 | 45–83 | 400 | — | 95.9 | 3.2 | 96.8/3.2 |
| Heel (3%) | α-Pinene | 2 | 61–86 | " | 0.1 | 95.6 | 3.4 | 96.6/3.4 |
| Heel (1%) | α-Pinene | 6 | 72–96 | " | 1.3 | 92.4 | 5.5 | 94.4/5.6 |
| Heel (1.5%) | ½ hypo-treated α-pinene | 8 | 71–85 | " | 1.1 | 95.4 | 2.4 | 97.5/2.5 |
| G-69 (3%) | Hypo-treated α-pinene | 24 | 30–60 | 200–600 | — | 95.8 | 3.0 | 97.0/3.0 |
| G-69 (3%) | Hypo-treated α-pinene | 30 | 30 | 200–400 | — | 97.5 | 1.9 | 98.1/1.9 |
| HCl SATURATED PINANE | | | | | | | | |
| G-69 (3%) | Pilot Plant prod. (69% α-pinene) + 5% HCl sat'd. pinane | 1 | 52–70 | 400 | — | (64.5) | (1.7) | 97.4/2.6 |

The use of cupric chloride as an additive at the 0.05% level (by weight of pinene) slowed the reaction with a slight effect on the product ratio, although a good product ratio was obtained. Reuse of the catalyst heel thus modified was also slow, but illustrates the ability to provide a good ratio. No effort was made to optimize these reactions with regard to rate. For instance, better rates are obtainable with more catalyst and higher temperature.

Hypochlorite treatment of the α-pinene raised the chloride level to about 100 ppm (as elemental chloride) based on pinene feed. Hydrogenation of this pinene was fast and yielded a good ratio (96.8/3.2). Reuse of the catalyst heel went quickly with a slightly reduced ratio, when used at either the 3% level or 1% level. Repoisoning (½% sodium hypochlorite-treated α-pinene) was achieved by mixing hypochlorite-treated feed with fresh α-pinene and yielded pinane with a 97.5/2.5 cis-:trans- ratio. A ratio of 98.1/1.9 was achieved in 30 hours' reaction at a lower temperature of about 30° C. using hypochlorite-treated feed.

HCl in the amount of about 5% based on the weight of pinene but added to the hydrogenation reaction mixture as a 5% HCl solution saturated with pinane, produced a starting material at the level of about 175 ppm chloride. Hydrogenation produced a good ratio of 97.4/2.6 in about 1 hours' time.

EXAMPLE 3

Several additional catalysts were investigated for use in the present reaction.

TABLE II
α-PINENE HYDROGENATIONS WITH VARIOUS CATALYSTS (CHLORIDE POISONED)

| Catalyst | Start. Matl. | Time | Temp. | H₂ Press. | α-P | cP | tP | c/t |
|---|---|---|---|---|---|---|---|---|
| HARSHAW Ni 0104P 3% Ni0104P | α-Pinene + 0.05% CCl₄ | 44-½ | 26–45 | 400 | 1.3 | 96.0 | 2.0 | 98.0/2.0 |
| CALSICAT Ni 210P 3% Ni210P | α-Pinene + 0.05% CCl₄ | 13 | 42–62 | 400 | — | 89.7 | 1.6 | 98.3/1.7 |
| " | " | 17 | 27–30 | " | — | 94.5 | 2.3 | 97.6/2.4 |
| HARSHAW Ni 1404P 3% Ni1404P | α-Pinene + 0.05% CCl₄ | 48-½ | 25–60 | 400 | — | 96.9 | 2.3 | 97.7/2.3 |
| GRACE 28 RANEY Ni 3% GRNi28 | α-Pinene + 0.05% CCl₄ | 50-⅔ | 25–48 | 400 | 5.5 | 92.0 | 2.0 | 97.9/2.1 |

Harshaw Ni 0104P — Despite slow rates this catalyst worked well with 0.05% CCl₄ modifier.

Calsicat 210P — Acceptable ratios were produced at reasonable rates with 0.05% CCl₄, but some by-product formation at high temperatures was observed. Suitable control of the higher temperature reaction can suppress by-product formation.

Harshaw Ni 1404P — Slow reaction rate with 0.05% CCl₄ produced an acceptable ratio.*

Grace 28 Raney Ni — Treatment with 0.05% CCl₄ improved the ratio greatly over the use of no modifier, but rate was slow.*

*No attempt was made to optimize the reaction rate, for instance with more catalyst or higher temperatures.

What is claimed is:

1. In the stereoselective hydrogenation of α-pinene to cis-pinane which comprises hydrogenating α-pinene under hydrogenation conditions at hydrogenation pressures and temperatures with a nickel hydrogenation catalyst, the improvement to achieve increased stereoselectivity which comprises carrying out said hydrogenation in the presence of a nickel catalyst which has an effective fraction of its reactive surfaces inactivated.

2. The hydrogenation process of claim 1 wherein said nickel hydrogenation catalyst is treated with a halogen-containing modifying agent.

3. The process of claim 2 wherein said modifying agent is an organic halogen.

4. The process of claim 2 wherein said modifying agent is an organic chloride.

5. In the stereoselective hydrogenation of α-pinene to cis-pinane which comprises hydrogenating α-pinene under hydrogenation conditions at hydrogenation pressures and temperatures with a nickel hydrogenation catalyst, the improvement for obtaining increased stereoselectivity which comprises carrying out said hydrogenation in the presence of a nickel catalyst which is treated with a chlorine-containing compound selected from the group consisting of sodium hypochlorite, hydrogen chloride, cupric chloride and carbon tetrachloride employing sufficient chlorine-containing compound to inactivate an effective fraction of the nickel catalyst reactive surfaces.

\* \* \* \* \*

UNITED STATES PATENT AND TRADEMARK OFFICE
CERTIFICATE OF CORRECTION

PATENT NO. : 4,018,842
DATED : April 19, 1977
INVENTOR(S) : Levy A. Canova

It is certified that error appears in the above-identified patent and that said Letters Patent are hereby corrected as shown below:

Column 1, in the equation, the formula for cis-pinane hydroperoxide should be as follows:

cis-pinane
hydroperoxide

Column 3, line 37, change "of" to --or--; line 58, change "used" to --and--.
Column 4, line 51, change "$CuSO_2$" to --$CuSO_4$--.
Column 5, line 38, change "30o" to --300--.
Column 6, line 5, after "pinane", insert --with a cis-/trans- ratio of 97:3 (about 95% cis-pinane--; line 40, change "4000 psig" to --400 psig--; line 53, change "temperatures" to --temperature--.

Signed and Sealed this nineteenth Day of July 1977

[SEAL]

Attest:

RUTH C. MASON
Attesting Officer

C. MARSHALL DANN
Commissioner of Patents and Trademarks